United States Patent [19]
Gaylord, Jr.

[11] 3,937,218
[45] Feb. 10, 1976

[54] DECUBITUS PAD

[75] Inventor: John F. Gaylord, Jr., Matthews, N.C.

[73] Assignee: Medical Specialties, Inc., Charlotte, N.C.

[22] Filed: July 29, 1974

[21] Appl. No.: 492,890

[52] U.S. Cl. .............................................. 128/149
[51] Int. Cl.² ......................................... A61B 19/00
[58] Field of Search ...... 128/80 R, 80 C, 82, 132 R, 128/149, 153, 157, 164–166.5, 169, 171, 299; 2/2, 16, 24, 61, 62

[56] References Cited
UNITED STATES PATENTS

| 2,377,339 | 6/1945 | Greene | 2/24 |
|---|---|---|---|
| 2,550,461 | 4/1951 | Fick | 2/16 |
| 2,603,786 | 7/1952 | Haines | 2/24 |
| 2,626,394 | 1/1953 | Davis | 2/24 |
| 2,690,747 | 10/1954 | Frallic | 128/165 |
| 2,759,189 | 8/1956 | Cole | 2/24 |
| 3,011,494 | 12/1961 | McGowan | 128/149 |
| 3,216,417 | 11/1965 | Posey | 128/165 |
| 3,322,118 | 5/1967 | Sotherlin | 128/149 |
| 3,374,785 | 3/1968 | Gaylord | 128/75 |
| 3,406,406 | 10/1968 | Lutz | 128/165 |
| 3,508,544 | 4/1970 | Moore et al. | 128/149 |
| 3,648,291 | 3/1972 | Pankers | 2/16 |
| 3,670,725 | 6/1972 | Gaylord, Jr. | 128/149 |
| 3,693,619 | 9/1972 | Williams | 128/157 |
| 3,721,237 | 3/1973 | Alessio | 128/149 |
| D195,191 | 5/1963 | Marvid | D3/26 |

FOREIGN PATENTS OR APPLICATIONS

| 522,718 | 6/1940 | United Kingdom | 2/24 |

*Primary Examiner*—Robert W. Michell
*Assistant Examiner*—Rick Opitz
*Attorney, Agent, or Firm*—Parrott, Bell, Seltzer, Park & Gibson

[57] ABSTRACT

A protective pad adapted for being positioned on an elbow or heel of a bedridden patient for protecting against the development of bedsores. The pad includes a scoop-shaped body member of cushioning material having a concave inner surface thereon defining an elbow or heel receiving pocket, a pair of straps extending in spaced apart relation from a rear portion of the body member and being of a length sufficient to permit positioning the straps across the body member for overlyingly engaging the limb of a patient, and a pair of fasteners carried by a front portion of the body member for releasably securing an end portion of each strap to the front portion of the body member. The fasteners are positioned in spaced apart relation on the body member and are adapted for securing the straps in overlapping crossed relation overlying the limb of the patient whereby the straps facilitate maintaining the body member in conforming relation on the limb of the patient while allowing free movement of the limb and while avoiding constriction of the limb as would reduce blood circulation therein.

8 Claims, 6 Drawing Figures

U.S. Patent  Feb. 10, 1976  3,937,218
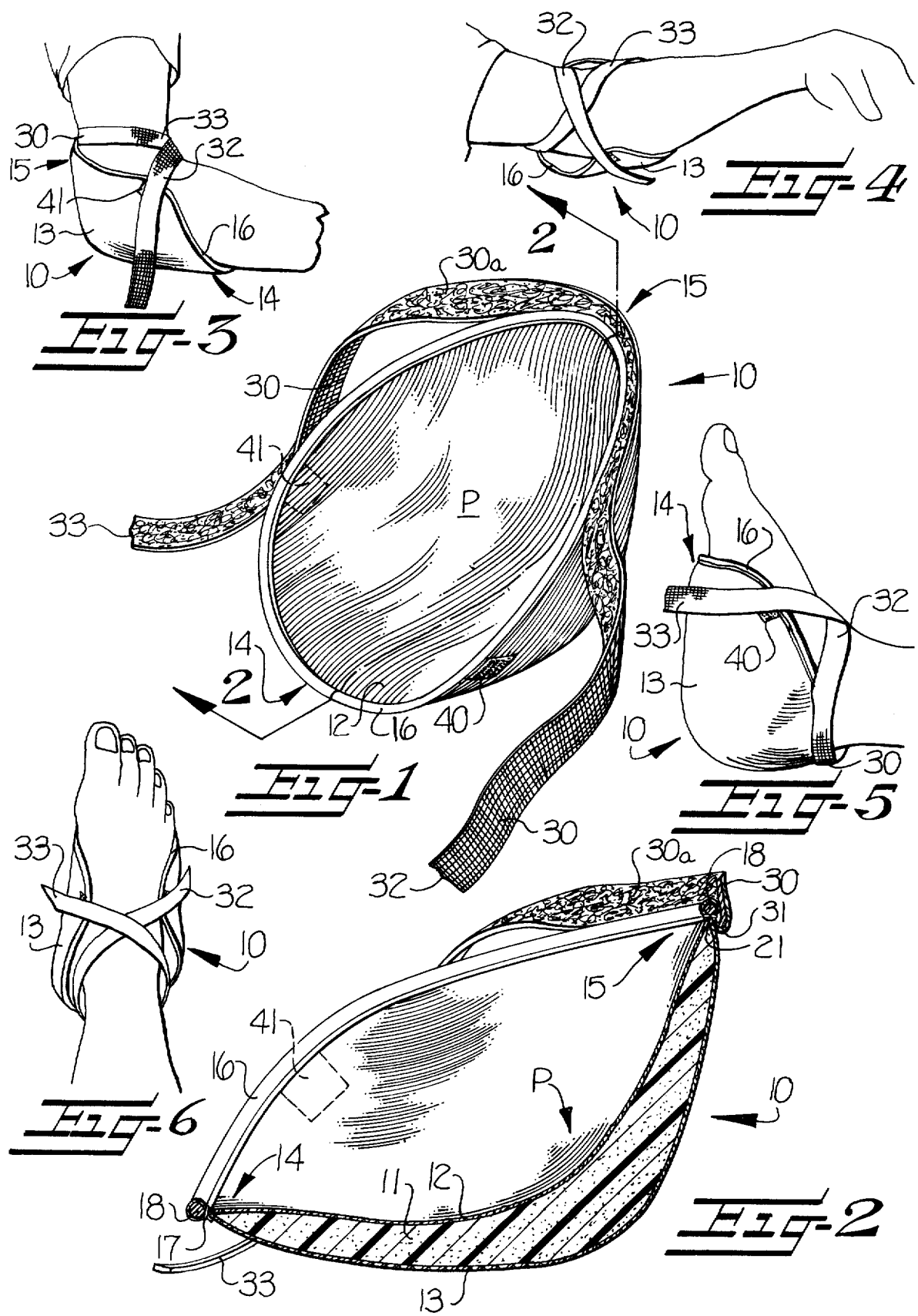

DECUBITUS PAD

This invention relates to a protective pad adapted for being worn on an elbow, heel or like body portion of bedridden patients.

Various types and forms of protective pads have been proposed for use by patients, particularly elderly patients who are confined to bed for extended periods of time during an illness or convalescence, for protecting portions of the patient's body, such as elbows and heels, from pressure and abrasive contact with the bed, which frequently contribute to the development of decubitus ulcers or bedsores. Such prior pads are usually specifically designed to be positioned to overlie one particular portion of the body, and they typically comprise a padded cushion member such as polyester fiber floss adhesively secured to a backing fabric. The cushion member is adapted to be folded, bent or seamed so as to be adapted to receive the intended body member therein. Where the pad is intended for use on the heel, or the elbow, one or more straps are generally provided on the cushion member for extending across the arm or leg of the patient to maintain the padded cushion member in position.

Pads of the types described above, while serving to cushion the body member have not been entirely satisfactory since they are undesirably bulky and do not conform well to the arm or leg, and are uncomfortable when worn for extended periods of time. Further, the straps employed for securing the pad to the elbow or heel tend to restrict movement of the patient's arm or leg and to impede blood circulation therein. This causes further discomfort and also contributes to the development of decubitus ulcers. Still further, a few patients suffer an allergic reaction to the commonly employed pads of the polyester floss type, and such pads do not possess adequate porosity or breatheability, and they have proven to be irritating to the skin of a wearer by holding moisture, such as perspiration and the like, against the skin.

With the foregoing in mind, it is a primary object of this invention to provide a protective pad which may be applied to either an elbow or heel of a patient, and which is comfortable to wear for extended periods of time.

It is another object of the present invention to provide a protective pad of the described type which possesses sufficient porosity to permit ventilation of the underlying skin of the wearer, which is non-allergenic, and which may be repeatedly laundered without damage to the pad.

It is a more specific object of the invention to provide a protective pad adapted to be positioned on either an elbow or heel of a patient, and wherein the protective pad includes a body member of cushioning material integrally formed with a concave surface thereon defining an elbow or heel receiving pocket and wherein the body member is thicker in medial portions thereof than along peripheral edge portions thereof so as to provide additional padding for the elbow or heel positioned in the pocket while avoiding undue bulkiness of the body member.

It is a further object of this invention to provide a protective pad adapted for being positioned on either an elbow or heel of a patient and wherein an improved arrangement of straps is provided for securing the protective pad to the elbow or heel while providing freedom of movement of the limb of the patient and while also avoiding restricting blood circulation in the limb.

In accordance with the above objects, the protective pad of this invention, in its preferred form, includes a scoop-shaped body member of cushioning material having a concave inner surface thereon defining an elbow or heel receiving pocket, a pair of straps extending in spaced apart relation from a rear portion of the body and being of a length sufficient to permit positioning the straps across the body member for overlyingly engaging the limb of the patient, and a pair of fastener means carried by the body member on a front portion thereof for releasably securing an end portion of each of the straps to the front portion of the body member. The pair of fastener means are positioned in spaced apart relation on the body member and are located for securing the straps in overlapping crossed relation overlying the limb of the patient so that the straps are thereby adapted for maintaining the body member in position on the limb of the patient while allowing free movement of the limb and while avoiding constriction of the limb as would reduce blood circulation therein. The body member includes a scoop-shaped molded porous core of unitary construction formed from discrete particles of polyurethane foam bonded together and a porous covering surrounding the core. The scoop-shaped core has a greater thickness in medial portions thereof than along peripheral edge portions thereof so as to provide additional padding for the elbow or heel positioned in the pocket of the body member while avoiding undue bulkiness of the body member.

Some of the objects of the invention having been stated, others will appear as the description proceeds, when taken in connection with the accompanying drawings, in which FIG. 1 is a perspective view of a protective pad in accordance with this invention;

FIG. 2 is a vertical sectional view of the pad taken substantially along line 2—2 of FIG. 1;

FIG. 3 is a side view of the protective pad as worn on the elbow of a patient;

FIG. 4 is a top view of the protective pad as worn on the elbow of a patient and showing the straps of the pad in the overlapping crossed relation across the cubital area of the arm;

FIG. 5 is a side view of the protective pad as worn on the heel of a patient; and FIG. 6 is a top view of the protective pad as worn on the heel of a patient and showing the straps of the pad in overlapping crossed relation across the instep of the foot.

Referring now more particularly to the drawings wherein like reference characters are used throughout to indicate like parts, the protective pad includes a body member, generally indicated by reference character 10, which is of curved, somewhat scoop-like shape having a concave inner surface thereon defining a pocket P adapted for receiving the elbow or heel of the wearer therein, and a pair of straps 32, 33 adapted for maintaining the body member 10 in position on the arm or leg of the wearer.

Referring to FIG. 2, body member 10 includes a core 11 having a generally circular peripheral outline and being formed of resilient flexible cushioning material which is of generally converging concavo-convex cross-sectional configuration. The core thus has a greater thickness in the medial portions thereof where the elbow or heel receiving pocket P is located than along the periphery of the core so as to provide additional padding for the elbow or heel where it is needed most while avoiding bulkiness of body member 10 particularly along the periphery or edge thereof. Also as seen in FIG. 2, the pocket P of the core 11 has a substantial depth which approximates one-half the overall diameter of the periphery of the core to thereby substantially fully surround and enclose the elbow or heel of the patient therein as hereinafter further explained. Core 11 is preferably formed of a porous foam material for providing breatheability and comfort during extended periods of wear. However, the core may also be formed of other materials such as fibrous padding material, if desired. When formed of foam material, the core preferably comprises discrete particles of polyurethane foam which are bonded together with a suitable binder during a molding operation, as described later.

The inner concave and outer convex surfaces of body member 10 respectively comprise sheets 12 and 13 of porous covering material which are preferably bonded to core 11 in conforming relation to the contoured inner and outer surfaces thereof to provide a unitary structure having a neat appearance even when deformed or flexed. Stretch fabrics are particularly suitable for use as a covering material because of their ability to conform to the shape of the core during use. For example, fabrics knitted from stretch yarns have been suitably employed as the covering material. Yarns of a hydrophobic material such as nylon are preferred since they serve to conduct moisture and perspiration away from the wearer and thus facilitate maintaining the skin free from irritation. Such yarns are also desirable since the resulting fabric has a low coefficient of friction, and the pad thus slides easily on the sheets of the bed.

In producing the body member 10, it has been found advantageous to mold the foam core 11 while simultaneously applying and bonding the sheets 12 and 13 of covering material thereto. A vacuum molding apparatus is preferably employed having a cooperating pair of male and female molding dies of suitable shape for forming the core in the desired convexo-concave form. In forming the foam core, common or virgin polyurethane foam is employed which is shredded or otherwise formed into discrete particles and which is thereafter mixed with a suitable binder such as about 4 percent by weight of base form polyester-type polyurethane and heated to form a tacky mass. After positioning sheets 12, 13 of covering material overlying the male and female molding dies, the molding composition is placed in the vacuum molding apparatus and a vacuum is thereafter drawn on the mass to form the same into the desired shape. The mass is thereafter cured, as by subjecting to steam, to form a resilient core of rebonded light polyurethane foam with sheets 12, 13 lightly bonded to the outer and inner surfaces thereof. The same binder which bonds the foam particles together also serves to lightly bond sheets 12, 13 to the core without undesirably affecting the softness of the fabric sheets. The thus formed core typically has a density of about 3–4 pounds per cubic foot, and the resulting laminated structure is air permeable and non-irritating to the skin, and is capable of withstanding repeated launderings so that it may be kept clean and sanitary at all times.

The scoop-shaped configuration of body member 10 is particularly adapted for protectingly surrounding an elbow or heel and for being worn on an arm or leg comfortably for extended periods of time. As illustrated, the body member 10 includes a front portion 14 wherein the walls thereof extend generally horizontally or slope upwardly gradually, and a rear portion 15 wherein the walls are of considerably steeper slope and extend sharply upwardly. Opposite sides of halves of the body member are generally symmetrical, with the plane of symmetry extending generally vertically through both the front and rear portions 14, 15 of the body member. As illustrated in FIG. 1, the plane of symmetry of body member 10 would pass through the section line 2—2, and FIG. 2 illustrates one of the two generally symmetrical halves of the body member 10.

As illustrated, sheets 12 and 13 are positioned surrounding core 11 with the raw edges of the sheets overlying one another along the edge or periphery of body member 10 at the juncture of the concave inner and convex outer surfaces thereof. A narrow seam binding strip or tape 16 is positioned overlying the raw edges of the two sheets 12, 13 of fabric and the entire assembly is then secured by stitching 17. The stitching 17 is preferably spaced a short distance from the edge of body member 10 so as to pass through the seam binding strip 16, through the two sheets 12, 13 of fabric and also through a portion of the edge of core 11, pinching the same so as to form a rounded padded bead 18 along the peripheral edge of the body member 10.

As illustrated in FIG. 1, the protective pad also includes an elongate strip 30, preferably formed of conventional flexible woven webbing material. A medial portion of strip 30 is secured along a portion of one longitudinal edge 31 thereof to the rear portion 15 of body member 10. More particularly, strip 30 is positioned beneath the rounded bead 18 at the rear portion 15 of the body member, and edge 31 thereof is secured to the body member by a second line of stitching 21 (FIG. 2) substantially overlying stitching 17. Stitching 21 secures strip 30 to the body member 10 for a short distance along the rear portion 15 thereof, generally not exceeding about one-third the circumference of the body member along the edge thereof, and preferably corresponding to about one-fourth the circumference. When secured in this manner, the distal portions of strip 30 form a pair of pliable binding elements or straps 32, 33 whose innermost portions extend generally tangentially from the edge of body member 10 to facilitate positioning the same in overlapping crossed relation, as described below. Straps 32, 33 are of a length sufficient to permit positioning the same across the body member for overlyingly engaging the limb of the patient and maintaining body member 10 in position there. After stitching, strip 30 is turned up as illustrated in FIG. 2 so that edge 31 is lowermost and the cushioned rounded bead 18 is positioned between the strip and the limb of the patient for cushioning the limb.

A pair of fastener means 40, 41 are provided on the front portion 14 of body member 10 for releasably securing the end portions of straps 32, 33 to the body member. In the illustrated embodiment, this fastener means comprises short strips of conventional hook-type Velcro fastener material sewn or otherwise suitably secured to the outer convex surface of the body member. The inner surface of strip 30 is provided, over at least the distal portions thereof, with the conventional type of soft fibrous Velcro fastener material 30a which is adapted for being engaged by the cooperating hook-like Velcro fastener elements on the body member. Obviously, other suitable fastener means, such as buckles, may be employed if desired.

Fastener means 40, 41 are located on opposite halves of body member 10 closely adjacent the edge thereof and are spaced apart from one another so as to be positioned on opposite sides of the patient's lower arm or foot. Fastener members 40, 41 are thereby adapted for securing a strap from the opposite side or half of the body member, as noted in more detail below. It will also be observed that the edge of body member 10 flares or bows upwardly on each side thereof between the fastener means 40, 41 and the point where each strap is secured to the body member. This flare or bow effectively deepens the elbow or heel receiving pocket P and facilitates maintaining the elbow or heel in position therein. Further, since the straps are arranged so as to extend from the rear portion 15 of the body member 10 diagonally across the same to the front portion 14 thereof, the strap arrangement serves to pull the front and rear portions closer together, further deepening the elbow or heel receiving pocket P while also pulling the body member 10 into conforming relation with the arm or leg of the wearer.

If desired, instead of using a separate seam binding strip 16 and elongate strip 30 as illustrated, a single elongate piece or strip of material may be employed for covering the raw edges of fabric sheets 12, 13 and for also defining straps 32, 33. In this alternate form, an elongate strip of material has a medial portion thereof stitched along the entire periphery or edge of the body member 10 to cover all the raw edges of fabric sheets 12, 13 and overlaps itself for a short distance at the rear portion 15 of the body member 10. The distal or end portions of the piece or strip of material extend outwardly from the body member in spaced apart relation at the rear portion 15 thereof to form a pair of pliable binding elements or straps. If desired, the binding elements or straps may be cord-like instead of flat, as in the illustrated embodiment. As in the illustrated embodiment, the innermost portions of the straps extend generally tangentially to the peripheral edge of the body member. If desired, the entire piece or strip of material forming the straps may be formed from a soft fibrous material of the type adapted for being engaged by the hook-like fastener elements on body member 10.

As seen in FIGS. 3 and 4, the protective pad is worn on the arm of a patient with the elbow thereof positioned in pocket P and with the rear portion 15 of body portion 10 positioned against the upper portion of the arm. Straps 32, 33 extend forwardly from behind the upper arm and diagonally cross the arm with an end portion of each strap being releasably secured to the front portion 14 of body member 10 by fastener members 40, 41. The straps 32, 33 are thus positioned in overlapping crossed relation across the cubital area of the arm and loosely engage the same for maintaining the body member 10 in position on the elbow. By extending across the arm in this manner, the straps permit free movement of the arm within body portion 10 while avoiding impingement upon the exposed antecubital veins in the arm as might otherwise restrict blood circulation in the arm. Further, as noted above, the forwardly extending strap arrangement serves to deepen the pocket P and facilitate maintaining the body member 10 in conforming relation on the arm.

As seen in FIGS. 5 and 6, the protective pad is worn on the foot by positioning the heel of the patient in pocket P with the rear portion 15 of body member 10 positioned against the Achilles tendon and with the front portion 14 of the body member being positioned against the sole of the foot. The straps extend forwardly from opposite sides of the ankle and diagonally cross the instep or arch of the foot. As noted above, the overlapping crossed relation of the straps permits free movement of the foot within the body member 10 while maintaining the body member in conforming relation on the foot without restricting blood circulation in the foot.

In the drawings and specification, there has been set forth a preferred embodiment of the invention, and although specific terms are employed, they are used in generic and descriptive sense only and not for purposes of limitation.

That which is claimed is:

1. A protective pad adapted to be positioned on an elbow or heel of a patient and characterized by providing freedom of movement of the limb of the patient and avoiding restricting circulation in the limb, said pad comprising a core of resilient foam material having a generally circular peripheral outline and generally converging concavo-convex cross-sectional configuration such that the concave inner surface defines a smoothly curved elbow or heel receiving pocket having a depth approximating one-half the overall diameter of the core to substantially fully surround and enclose the elbow or heel of the patient therein, a sheet of fabric smoothly overlying and bonded to each of the concave and convex surfaces of said core, a pair of spaced apart straps attached to said pad and extending tangentially and in opposite directions from a rear portion of the periphery of said core and with each strap being of a length sufficient to permit positioning of the strap across the core and over the limb of the patient, and a pair of fastener elements attached to said pad on a front portion of the periphery thereof for releasably securing the end portion of each strap to the front portion of said core, said pair of fastener elements being positioned in spaced apart relation such that the straps may be secured in overlapping crossed relation over the limb of the patient, said straps being thereby adapted to facilitate maintaining the pad in conforming relation on the limb of the patient while allowing free movement of the limb and avoiding constriction of the limb as would reduce circulation therein.

2. The protective pad as defined in claim 1 wherein said pair of fastener elements are located on the outer convex surface of said pad, and each comprises a multiplicity of hook-like fasteners which are adapted to releasably secure an end portion of said strap thereto.

3. The protective pad as defined in claim 2 further comprising a narrow seam binding strip extending about the periphery of said core and overlying the edges of said sheets, and stitching extending through a portion of the peripheral edge of said core and said sheets for securing said strip thereto.

4. The protective pad as defined in claim 1 wherein each of said sheets comprises a resilient fabric material which is bonded to the adjacent surface of said core throughout the full area thereof.

5. The protective pad as defined in claim 4 wherein each of said sheets further comprises a knit fabric material formed of polymeric yarns to facilitate the passage of moisture and perspiration therethrough.

6. The protective pad as defined in claim 4 wherein said core is formed of bonded discrete particles of polyurethane foam material and has a density of between about three to four pounds per cubic foot.

7. The protective pad as defined in claim 4 wherein said straps comprise a unitary strip of fabric having the medial portion thereof joined to the periphery of said core.

8. The protective pad as defined in claim 4 wherein said core has generally symmetrical opposite halves with each half having front and rear portions and with the rear portion of each half having walls of greater slope than the walls of the front portion thereof.

* * * * *